United States Patent [19]
Lemke et al.

[11] Patent Number: 6,033,876
[45] Date of Patent: Mar. 7, 2000

[54] ANTI-CD30 ANTIBODIES PREVENTING PROTEOLYTIC CLEAVAGE AND RELEASE OF MEMBRANE-BOUND CD30 ANTIGEN

[75] Inventors: Hilmar Lemke, Achterwehr; Hinrich-Peter Hansen, Kiel, both of Germany

[73] Assignee: Boehringer Mannheim GmbH, Mannheim, Germany

[21] Appl. No.: 08/860,727

[22] PCT Filed: Jan. 11, 1996

[86] PCT No.: PCT/EP96/00098

§ 371 Date: Sep. 26, 1997

§ 102(e) Date: Sep. 26, 1997

[87] PCT Pub. No.: WO96/22384

PCT Pub. Date: Jul. 25, 1996

[30] Foreign Application Priority Data

Jan. 18, 1995 [EP] European Pat. Off. .............. 95100591

[51] Int. Cl.$^7$ ..................... A61K 39/395; C12N 15/13; G01N 33/53
[52] U.S. Cl. ..................... 435/69.6; 435/69.7; 435/7.23; 435/334; 435/344; 424/133.1; 424/138.1; 424/144.1; 424/155.1; 530/387.3; 530/387.7; 530/388.22; 530/388.8
[58] Field of Search ............................... 424/133.1, 138.1, 424/144.1, 155.1; 530/387.3, 387.7, 388.22, 388.8; 435/334, 344, 7.23, 69.6, 69.7

[56] References Cited

U.S. PATENT DOCUMENTS 5,165,923  11/1992  Thorpe et al. .

FOREIGN PATENT DOCUMENTS

239400 A2  9/1987  European Pat. Off. .
42 05 938  9/1993  Germany .

OTHER PUBLICATIONS

Linnartz, et al., *Annals of Hematology*, vol. 67 (suppl.) (Oct. 10–13) 1993, p. A77 XP 000567763, abstract 298, "Development of new ricin A–chain immunotoxins for the treatment of hodgkins's disease using high–affinity mooclonal antibodies against the CD–30 antigen".

International Publication No. WO 91/07437 published May 30, 1991.

Falini, et al., *British Journal of Hematology*, vol. 82, No. 1 (1 992), pp, 38–45, "In vivo targeting of Hodgkin and Reed–Sternberg cells of Hodgkin's disease with monoclonal antibody Ber–H2 (CD30): Immunohistological evidence".

Horn–Lohrens, et al., *International Journal of Cancer*, vol. 60, No. 4 (Feb. 8) 1995, pp. 539–544, "Shedding of the soluble form of CD30 from the Hodgkin–analogous cell line L540 is strongly inhibited by a new CD30–specific antibody (Ki–4)".

Schnell, et al., *International Journal of Cancer*, vol. 63, No. 2 (Oct. 9) 1995, pp. 238–244, "Development of new ricin A–chain immunotoxins with potent anti–tumor effects against human Hodgkin cells in vitro and disseminated Hodgkin tumors in SCID mice using high–affinity monoclonal antibodies directed against the CD30 antigen".

Hansen, et al., *International Journal of Cancer*, vol. 63, 1995, pp. 750–756, "A zinc metalloprotein is responsible for the release of CD30 on human tumor cell lines".

Riechmann et al Nature vol. 332 323, Mar. 1988.

Queen et al Proc Natl Acad Sci USA vol. 86 10029–10033, Dec. 1989.

Engert et al Cancer Research vol. 50 4–88, Jan. 1990.

Engert et al Cancer research vol. 50 2929–2935, May 1990.

Paul, WE Fundamental Immunology p. 242, 1993.

Rudikoff et al Proc Natl Acad Sci USA vol. 79 1979, 1982.

*Primary Examiner*—Julie Burke
*Attorney, Agent, or Firm*—Nikaido Marmelstein Murray & Oram LLP.

[57] ABSTRACT

An antibody which binds to the CD30 antigen and a) inhibits the release of sCD30 from Hodgkin's disease cells, and b) does not bind to B cell non-Hodgkin's lymphomas or plasma cells. An example of such antibodies are the antibodies secreted from hybridoma cell line DSM ACC 2204. The antibodies may be used for diagnosis, or conjugated to a toxin to produce an immunotoxin.

16 Claims, No Drawings

ANTI-CD30 ANTIBODIES PREVENTING PROTEOLYTIC CLEAVAGE AND RELEASE OF MEMBRANE-BOUND CD30 ANTIGEN

This application is a 35 U.S.C. §371 National Stage filing of PCT/EP96/00098, filed Jan. 11, 1996.

The invention comprises high-affinity Hodgkin's disease cell specific anti-CD30 antibodies which prevent proteolytic cleavage and release of membrane-bound CD30 antigen, a method of production and the use of said antibodies.

INTRODUCTION

The CD30 activation marker was originally discovered as the Hodgkin-associated Ki-1 antigen (Schwab et al. (1982) (1)). CD30 is a membrane glycoprotein with a molecular weight of 120 kDa (Froese et al. (1987) (8)). A soluble form of the CD30 (sCD30) is released from cell membranes (Hansen et al. (1989) (2)) which is detectable in sera of Hodgkin patients (Josimovic-Alasevic et al. (1989) (3), Pfreundschuh et al. (1990) (4)) and the serum levels of the sCD30 correlate with the severity and the clinical stage of the disease (Pizzolo et al. (1990) (5)). sCD30 is a cleavage product of the cell surface-bound CD30 molecule, as it could be shown that the glycosylation pattern of CD30 and sCD30 is identical. CD30 is cleaved by a specific acting protease.

The membrane-associated CD30 antigen is regarded as a possible target for treatment of Hodgkin's-diseased patients with immunotoxins. However, the efficacy of the various antibody-toxin conjugates show rather big differences (Engert et al. (1990) (6)). Moreover, the CD30-specific monoclonal antibody (mAb) Ki-1 enhanced the release of the sCD30 from the Hodgkin-derived cell lines L428 and L540 as well as from the CD30+ non-Hodgkin's lymphoma cell line Karpas 299 (Hansen et al. (1991) (7)).

Shedding of CD30 molecules from the cell surface of tumour cells weakens or may even make obsolete the use of this antibody especially in the form of immunotoxins in the treatment of cancer, since such antibodies bind to CD30 as well as to sCD30.

The conjugate of antibody Ki-1 with the Ricin A-chain, for instance, was a rather ineffective immunotoxin and it was concluded that this ineffectiveness was due to the rather low affinity of antibody Ki-1 (Engert et al. (1990) (6)). Two other reasons may also account for the weak toxicity of Ki-1-Ricin A-chain conjugates: a) Antibody Ki-1 enhanced the release of the sCD30 from the Hodgkin-derived cell lines L428 and L540 as well as from the CD30+ non-Hodgkin's lymphoma cell line Karpas 299 Hansen et al. (1991) (7)); b) the relatively great distance of the Ki-1 epitope from the cell membrane is also not favorable for the construction of potent immunotoxins (Press et al. (1988) (11), May et al. (1990) (12)).

At the Fourth Workshop on Leukocyte Differentiation Antigens in Vienna in February 1989, monoclonal antibodies were submitted by three different laboratories and finally characterized as belonging to the CD30 group. Co-cultivation experiments by the inventors of L540 cells with various antibodies according to the state of the art, followed by the isolation of sCD30 from culture supernatant fluids, revealed that the release of the sCD30 was most strongly increased by antibody Ki-1, and weakly enhanced by the antibody HeFi-1, whilst being more strongly inhibited by the antibody Ber-H2. However, the antibody Ber-H2 also labels a subpopulation of plasma cells (R. Schwarting et al. (1989) (10)) and G. Pallesen (9) describes, on page 411, that Ber-H2 is cross-reacting with an epitope of an unrelated antigen which is altered by formaldehyde. Therefore, in the state of the art, no anti-CD30 antibody is known which does not release sCD30 and is specific for Hodgkin and Reed-Sternberg cells.

SUMMARY OF THE INVENTION

It was therefore the object of the invention to provide new CD30-specific antibodies which do not promote the release of the sCD30, but inhibit the formation of the sCD30 instead and thus would possibly allow the formation of powerful immunotoxins. In the present invention there is described the production and reactivity of new CD30-specific antibodies with special reference to the relative positions of the epitopes recognized by these and other established anti-CD30 antibodies on the extracellular part of the CD30 molecule. The new antibodies according to the invention exhibit a nearly complete inhibition of the formation of the sCD30 and do not bind to a considerable extent to plasma cells or B cell non-Hodgkin's lymphomas and are therefore specific for Hodgkin and Reed Sternberg cells.

By means of the process according to the present invention it is possible to obtain antibodies having the aforementioned properties. An example of an antibody which can be obtained with the help of the process according to the present invention is the monoclonal antibody Ki-4 secreted by the hybridoma cell line DSM ACC 2204.

DETAILED DESCRIPTION OF THE INVENTION

The present invention provides antibodies which bind to the CD30 antigen and
 a) release sCD30 from Hodgkin's disease cells to an amount of, or less than, about 10% referred to the release found without an addition of antibodies;
 b) do not bind to B cell non-Hodgkin's lymphomas or plasma cells to a considerable extent.

As used herein the term "release sCD30" means the shedding of CD30 molecules from the cell surface of tumour cells. This release is reduced to a considerable extent using the antibodies of the invention compared to the shedding which is found in the case of CD30+ Hodgkin's cells in vitro und in vivo without antibodies. Release (shedding) of sCD30 can be tested according to the method described by Hansen et al. (1989) (2). When applying this method it was found that, using the antibodies according to the invention, the release of sCD30 from Hodgkin's disease cells could be reduced to 10% or less. Depending on the chasing time, antibody Ki-4 inhibited the shedding of the sCD30. Up to 16 h the shedding was nearly completely inhibited, i.e. less than 1%. Thereafter, the amount of sCD30 could increase to maximally 10% compared to that of untreated control cells.

As used herein the term "do not bind to a considerable extent" means that a binding cannot be detected by the conventional methods of detecting such bindings which are known in the prior art. Customarily, immune precipitation is applied to determine the binding. The conventional limit of error in immune precipitation is about ≦5%. This implies that the term "do not bind to a considerable extent" means that a binding is not detectable by applying the conventional methods of immune precipitation having a limit of error of ≦5%.

As used herein "substantially pure" means that the species is a predominant species present (i.e. on a molar basis, it is more abundant than any other individual species in the composition) and preferably a substantially purified fraction, wherein said species comprises at least about 50% (on a molar basis) of all macromolecular species present. Generally, a substantially pure composition will comprise more than about 80 to 90% of all macromolecular species present in the composition. Most preferably, said species is purified to homogeneity (contaminant species cannot be detected in the composition by conventional detection methods), wherein the composition consists essentially of a single macromolecular species.

As used herein, the term "antibody" refers to a protein consisting of one or more polypeptides substantially encoded by antibody genes. The recognized antibody genes include the different constant region genes as well as the myriad antibody variable region genes. Antibodies may exist in a variety of forms, including, for example, Fv, Fab, and F(ab)$_2$ as well as single chains (e.g. Houston et al. (1988) (57) and Bird et al.(1988) (58) and, in general, Hood et al. (1984) (59) and Hunkapiller and Hood (1986) (60). Preferred antibodies according to the invention are monoclonal antibodies and fragments thereof having the same features in relation to the CD30 antigen interaction.

The antibody preferably comprises at least two light polypeptide chains and two heavy polypeptide chains. Each of the heavy and light polypeptide chains contains a variable region (generally the amino terminal portion of the polypeptide chain) which contains a binding domain which interacts with antigen. Each of the heavy and light polypeptide chains also comprises a constant region of the polypeptide chains (generally, the carboxyl terminal portion) which may mediate the binding of the antibody to host tissues or factors including various cells of the immune system, some phagocytic cells and a first component (Clq) of the classical complement system. Typically, the light and heavy polypeptide chains are complete chains, each consisting essentially of a variable region and a complete constant region. The variable regions of the antibody according to the invention can be grafted to constant regions of other isotypes. For example, a polynucleotide encoding the variable region of a Ki-4 heavy chain of the γ1-isotype can be grated to polynucleotide encoding the constant region of another heavy chain class (or subclass).

Moreover, one to several amino acid substitutions, especially conservative amino acid substitutions, generally can be made to the amino acid sequence of the heavy chain and/or light chain sequences of the present antibodies, without substantially interferring with the antigen binding, and in some embodiments, without substantially increasing the antigenicity of the antibody when injected into a human patient. In some variations, deletions or additions of one to several amino acids can be made. Typically, the amino acid substitutions, additions or deletions are made to constant regions or variable regions, framework sequences and to complementary determining sequences (CDR).

Conservative amino acid substitution is a substitution of an amino acid by a replacement of an amino acid which has similar characteristics (e.g. those with acidic properties: Asp or Glu). A conservative amino acid substitution should not substantially change the structural characteristics of the parent sequence. Examples of such polypeptide structures are described in Proteins, Structures and Molecular Principles, Creighton (editor), W. H. Freeman and Company, New York (1984) (61), Introduction to Protein Structure, C. Brandon and J. Tooze, Garland Publishing, New York (1981) (62) and Thornton et al. (1991) (63).

For example, single or multiple amino acid substitutions (preferably conservative amino acid substitutions) may be made in the naturally occurring sequence (preferably in the portion of the polypeptide which does not directly contact antigen).

With the antibodies according to the invention it is possible to find a great number of further antibodies which interact with CD30 in an analogous manner. Such antibodies are bindable to CD30 antigen in a manner equivalent to the antibodies according to the invention, especially Ki-4. Furthermore, these antibodies must be tested for the release of sCD30 from Hodgkin's disease cells, the antibodies and the cell lines, respectively, which release sCD30 to an amount of, or less than, 10%, referred to the release found without an addition of antibodies, are isolated, furthermore those cell lines which produce antibodies that bind to Hodgkin's disease cells but not to B cell non-Hodgkin's lymphoma or plasma cells are isolated.

By the term "antibodies bindable in an equivalent manner" there are to be understood antibodies in the case of which an epitope overlapping is detectable with the antibodies in question. The epitope overlapping can be detected with the help of a competitive test system. For this purpose, for example with the help of an enzyme immunoassay there is tested the extent to which the antibody competes with the known antibody for the binding to an immobilized CD30 antigen. For this purpose, an appropriately -immobilized antigen (e.g. a CD30+ cell such as L540 cells) is incubated with the antibody Ki-4 in labelled form and an excess of the antibody in question. By detection of the bound labelling there can easily be ascertained the extent to which the antibody in question can displace the definite antibody from the binding. If there is a displacement of at least 50% at the same concentration or at higher concentrations, preferably in the case of $10^5$-fold excess of the antibody in question, referred to Ki-4, then the epitope overlapping is present.

The antibodies can be used as whole monoclonal antibodies, fragments thereof (e.g. Fv, (Fv)$_2$, Fab, Fab', F(ab)$_2$), chimeric, humanized or human antibodies as long as they are binding to CD30 in a suitable manner. Short-chain antibody fragments containing only the CDR regions or parts thereof conferring the specific binding to CD30 are also suitable, especially if the antibody is a labelled one. Antibodies of the IgG1 isotype are preferred.

As to production of monoclonal antibodies see, for example, E. Harlow and D. Lane (1988) (45), Bessler et al. (1985) (46), Jung et al. (1985) (47) or Cianfriglia et al. (1993) (48).

The present invention also provides a process for the production of an antibody which binds to the CD30 antigen and a) releases sCD30 from Hodgkin's disease cells to an amount of, or less than, 10%, referred to the release found without an addition of antibodies;
b) does not bind to B cell non-Hodgkin's lymphomas or plasma cells to a considerable extent, wherein a mammalian species is immunized with a Hodgkin's disease cell line, anti-CD30 antibody producing B cells are isolated and fused with myeloma cell lines, the fused cell lines are isolated and tested for antibody activity against Hodgkin's disease cells and the release of sCD30 from Hodgkin's disease cells, the cell lines which produce antibodies that bind to Hodgkin's disease cell lines but not to B cell non-Hodgkin's lymphomas or plasma cells to a considerable extent and release sCD30 to an amount of, or less than, 10%, referred to the release found without an addition of antibodies, are isolated, monoclonal antibodies are produced from said cell lines and isolated, preferably to substantial purity.

There is preferred a process for the production of Mabs with a reduced immunogenicity in humans, wherein variable regions of Ki-4 are linked to constant regions of a human antibody.

The present invention also provides derivatives of antibodies according to the present invention, which possess the binding specificity thereof, but with modifications in the region which is not important for the antigen binding. These antibody derivatives can possibly be obtained from antibodies according to the present invention by the exchange of one or more constant domains and/or linkages with other molecules. Thus, for example, an exchange of constant domains for an isotype can be carried out where, for example, an antibody of class IgM can be converted into an antibody of class IgG, with maintenance of its antigen specificity. This isotype switch can take place by cell biological or molecular biological methods which are well-known (see, for example, P. Rothman et al, (1990) (13)).

The present invention is also concerned with the use of an antibody according to the present invention for the diagnosis or therapy of Hodgkin's disease. It is thereby preferred to use the antibody Ki-4 secreted by the cell line DSM ACC 2204.

Since the antibodies obtained by the process according to the present invention are bindable with surface-bound CD30 molecules but inhibit sCD30 release, they are outstandingly suitable for the qualitative or quantitative detection of Hodgkin's disease. The detection thereby takes place in the known manner by means of an immunological process of determination. Processes of this type are well-known and do not need to be further explained here. The antibodies obtained according to the present invention can thereby be used as unlabelled and/or immnobilized receptors.

In each case of such immunological method of diagnosis, there is evaluated a signal change following the binding of at least one antibody according to the invention, to which is bound a detectable label.

The diagnostic significance of the CD30 antigen is described, for example, by G. Pallesen (1990) (9).

The present invention also provides a process for therapy of Hodgkin's disease, wherein there is administered one or a mixture of several antibodies according to the present invention, optionally together with conventional pharmaceutical carrier, adjuvant, filling or additive materials.

For prevention of an immune response, it is preferred to use antibodies which resemble as closely as possible antibodies of human origin (Glassy and Dillman (1988) (39)). Preferably, there are used antibodies wherein the constant region of Ki-4 is further modified in that part or all of the non-CD30 binding sequences of said antibody are replaced by the corresponding sequences from a human variable region. Such antibodies are, for example, chimeric or humanized (CDR-grafted) antibodies. Such antibodies usually are manufactured from a rodent monoclonal antibody (see e.g. for review: Morrison (1992) (39); Winter and Milstein (1991) (40)). In a specifically preferred embodiment of the invention, tumour specific human antibodies (Borrebaeck et al. (1988) (41); Borrebaeck (1988) (42)) are used for therapeutic purposes. In addition, it is specifically preferred to prepare human Mabs via phage display libraries, as is described, for example, by Griffith et al. (1993) (43).

It is specifically preferred to use, for therapeutic purposes, cytotoxic antibodies which impart effector functions (ADCC, CDC) (Brüggemann et al. (1987) (44)).

Since the monoclonal antibodies obtained by the process according to the present invention bind to cell surface-bound CD30 antigen, they can be used for in vivo treatment in humans. Thus, the present invention also provides a pharmaceutical composition which comprises one or more antibodies according to the present invention, optionally together with conventional pharmaceutical carrier, adjuvant, filling or additive materials. The administration of a medicament according to the present invention is useful for the treatment of Hodgkin's disease.

A suitable dosage of the antibody according to the present invention for the treatment of Hodgkin's disease is about 1 to 10 mg/kg body weight, whereby this dosage possibly is to be repeatedly administered.

In another approach, the antibody or part of it is conjugated or translationally fused to a toxin molecule (immunotoxin), thus effecting specific killing of tumour cells (Brinkmann et al. (1991) (30); Pastan et al. (1991) (31); FitzGerald and Pastan (1989) (32)). In another preferred embodiment of the invention, bispecific antibodies are used for tumour therapy (Bonino et al. (1992) (33)), which may be constructed by in vitro reassociation of polypeptide chains, by hybrid hybridoma generation or by construction of diabodies (Holliger et al. (1993) (34); Holliger and Winter (1993) (35)).

With regard to immunotoxins, it is preferred to couple the antibody according to the invention to a toxin, such as, for example, Pseudomonas exotoxin, Diphtheria toxin or other toxins (FitzGerald and Pastan (1989) (32)). It is also preferred to couple the antibodies to chemotherapeutics, such as, for instance, doxorubicin, or to radioactively labelled substances which have a cytotoxic effect.

Conjugates of the antibodies according to the invention, in particular of human antibodies, for in vivo imaging, using, for instance, radioactive or fluorescent substances, are also preferred.

Immnunotoxins are conjugates of antibodies or of the antigen binding regions of antibodies with toxins or their effective fragments. Immunotoxins can be produced by either of two principally different methods:

In one method, an antibody or a fragment thereof (normally generated proteolytically, e.g. Fab-fragment) is chemically coupled in vitro to a toxin or toxin fragment. For practical reasons, the antibody part in this type of immunotoxin is either a complete antibody (consisting of two light and two heavy chains) or, more preferably, a Fab-fragment (consisting of one light chain and the VH- and CH1-regions of the heavy chain).

In another method, the immunotoxin is generated by recombinant DNA techniques, which leads in any case to a defined, homogeneous molecule. The size of the antibody part should be as small as possible to obtain a small immunotoxin with good tissue penetration. In this method, the smallest practically available antibody fragment is not the Fab-fragment, but the functional variable domain of an antibody, consisting of the VH-region of the heavy chain and the VL-region of the light chain only. VH- and VL-region (polypeptide chains each of about 100 amino acids) have to form a functional assembly, the variable domain, which confers antigen binding. In the absence of any of the remaining parts of an antibody, VH- and VL-region form very labile complexes only. Therefore, their complex is preferably stabilized by covalent bonds.

One possibility is to fuse on the DNA level VH-region, VL-region (or vice versa) and the toxin part. Upon expression, a single polypeptide chain is formed, wherein VH- and VL-region, being connected by a peptide linker, fold into a stable variable domain, while the toxin is fused e.g. to VL via a second peptide linker (see Brinkmann et al. (1992) (49)). The length of both peptide linkers is variable and may in some instances even be reduced to a single peptide bond. A molecule of this type has been termed a "single chain immunotoxin", analogous to the term "single chain antibody" or scFV, which is used for a single polypeptide chain containing both VH and VL connected by a peptide linker or bond.

Another possibility to stabilize the VH- and VL-assembly is described in Brinkmann et al. (1993) (50)). In this technique, amino acids on VH and VL were defined by computer aided modelling, which are closely adjacent in the VH-VL-complex. The naturally occurring amino acids in these positions were then on the DNA level replaced by a cystein each. To obtain a functional imnmunotoxin in this case, two separate polypeptide chains are expressed (in separate cells, e.g. prokaryotic cells, e.g. *E.coli*), one being the VH-region only, the other the VL-region fused by a peptide linker to the toxin part. These two polyeptide chains are mixed under appropriate conditions and thus assemble into a functional immunotoxin, where VH and VL in the variable antibody domain are connected by a disulfide bond between the two cysteins introduced by genetic engineering. The antibody part of this type of immunotoxin has been designated dsFV and the whole molecule consequently as "dsFV-immunotoxin".

Of course there exist additional possibilities to produce immunotoxins by recombinant DNA techniques, for instance by using the larger Fab-fragment (VH-CH1 non-covalently assembled to VL-CL, while one of them is fused by a peptide linker to the toxin). However, the possibilities described by Brinkmann et al. (1992) (49) and Brinkmann et al. (1993) (50) are to be preferred.

With respect to the toxin part of the immunotoxin, preferred fragments of the Pseudomonas exotoxin (PE) are PE38 and PE40 and derivatives thereof (I. Pastan et al., WO 92/07271 (28), WO 90/12592 (29)).

Single chain $F_v$-chain immunotoxin is preferably produced as a single polypeptide chain in *E.coli*, using the T7 RNA polymerase expression system. The polypeptide is obtained in an active form and has to be activated by in vitro renaturation.

Other methods for the production of peptide bonded single chain immunotoxins are described in WO 88/09344 (51). Single chain antibodies with a peptide linker between the light and the heavy chain are described in WO 88/01649 (52). The production of chimeric antibodies which comprises at least the variable regions of a heavy and light chain whereby one of these chains is linked by a peptide bond to a non-Ig molecule are described in EP-B 0 193 276 (53). The T7 RNA polymerase expression system is described in U.S. Pat. Nos. 7,648,971 (54), 4,952,496 (55) and 6,595,016 (56).

Polynucleotides of the invention and recombinantly produced anti-CD30 antibodies of the invention may be prepared on the basis of the sequence data according to methods known in the art and described in Sambrook et al. (1989) (64) and Berger and Kimmel (1987) (65). Polynucleotides of the invention are preferably formed from synthetic oligonucleotides.

Such recombinant polypeptides can be expressed in eukaryotic or prokaryotic host cells according to standard methods known in the art, preferably mammalian cells, such as lymphocyte cell lines, may be used as host cells. Typically, such polynucleotide constructs encode a complete human antibody heavy chain and/or a complete human antibody light chain having at least the amino acid sequences of Ki-4, heavy and/or light chain variable regions respectively. Alternative human constant region sequences (heavy and/or light chain) other than those naturally associated with Ki-4, antibody chains may be substituted, including human constant region isotypes, such alternative human constant region sequences can be selected by those of skill in the art from various reference sources, including, but not limited to, those listed in E. A. Kabat et al. (1987) (37). In one embodiment of the invention, a polynucleotide sequence encoding an antibody light chain comprising a human light chain, constant region with an amino terminal peptide linkage (i.e. an inframe fusion) to a variable region of the light chain of Ki4 and a corresponding heavy chain are expressed and form heavy/light chain dimers and other antibody types.

In general, prokaryotes can be used for cloning the DNA sequences encoding a Ki-4 antibody chain. *E.coli* is one prokaryotic host particularly useful for cloning the DNA sequences of the present invention. Alternatively, oligonucleotides may be synthesized chemically by a variety of methods, including phosphoramidite synthesis.

The polynucleotide constructs will typically include an expression control sequence operatively linked to the coding sequences, including naturally associated or heterologous promotor regions. Preferably, the expression control sequences will be eukaryotic promotor systems in vectors capable of transforming or transfecting eukaryotic host cells. Once the vector has been incorporated into the appropriate host, the host is maintained under conditions suitable for high level expression of the nucleotide sequences and the collection and purification of the antibodies according to the invention. As eukaryotic host cells, mammalian tissue cell cultures may also be used to produce the polypeptides of the present invention. Mammalian cells are actually preferred, because a number of suitable host cell lines capable of secreting intact heterologous proteins have been developed in the art and include the CHO cell lines, various COS cell lines, HeLa cells, myeloma cell lines, etc.

Typically, the polynucleotide sequences encoding the heavy and/or light chains of the antibody according to the invention are introduced into and expressed in glycosylating cells which glycosylate the antibody. As used herein "glycosylating cell" is a cell capable of glycosylating proteins, particularly eukaryotic cells capable of adding an N-linked "core oligosaccharide" containing at least one mannose residue and/or capable of adding an O-linked sugar to at least one glycosylation site sequence in at least one polypeptide expressed in said cell, particularly a secreted protein. Thus, a glycosylating cell contains at least one enzymatic activity that catalyzes the attachment of a sugar residue to a glycosylating site sequence in a protein of polypeptide and the cell actually glycosylates at least one expressed polypeptide. For example, but not for limitation, mammalian cells are typically glycosylating cells. Other eukaryotic cells such as insect cells and yeast may be glycosylating cells.

Once expressed, Ki-4 antibodies according to the invention can be purified according to standard procedures of the art, including HPLC purification, fraction column chromatography, gel electrophoresis, and the like (see generally, R. Scopes (1982) (36)).

The therapeutic compounds of this invention may be administered parenterally, such as intravascularly, intraperitoneally, subcutaneously, intramuscularily, using forms known in the pharmaceutical art. The active drug components of the present invention are used in liquid, powdered or lyophilized form and may be combined with a suitable diluent or carrier, such as water, a saline, aqueous dextrose, aqueous buffer, and the like. Preservatives may also be added.

Regardless of the route of administration selected, the compounds of the present invention are formulated into pharmaceutically acceptable dosage forms by conventional methods known to those skilled in the art. The compounds may also be formulated using pharmacologically acceptable acid or base addition salts. Moreover, the compounds or their salts may be used in a suitable hydrated form.

Regardless of the route of administration selected, a non-toxic but therapeutically effective quantity of one or more compounds of this invention is employed in any treatment. The dosage regimen for treating is selected in accordance with a variety of factors including the type, age, weight, sex and medical condition of the patient, type of tumour, the route of administration and the particular compound employed in the treatment. A physician of ordinary skill can readily determine and prescribe the effective amount of the drug required regarding known antibody therapy approaches. In so proceeding, the physician could employ relatively low doses at first, and subsequently, increased dose until a maximum response is obtained.

For therapeutic uses, a sterile composition containing a pharmacologically effective dosage of one or more antibodies according to the invention is administered to human patient for treating Hodgkin's disease. Typically, the composition will comprise a chimeric or humanized antibody which contains the CDR region of Ki-4 for reduced immunogenicity.

Pharmaceutical compositions comprising a Ki-4 antibody of the present invention are useful for topical or parenteral administration, i.e. subcutaneously, intramuscularly, intravenously or transdermally. The compositions for parenteral administration will commonly comprise a solution of a Ki-4 antibody dissolved in an acceptable carrier, preferably in an aqueous carrier.

A variety of aqueous carriers can be used, e.g. water, buffered water, 0.4% saline, 0.3% glycin, and the like. The solutions are sterile and generally of particulate matter. The compositions may be sterilized by conventional well-known techniques. The compositions may contain pharmaceutically acceptable auxiliary substances, such as are required to approximate physiological conditions, such as pH adjusting and buffer agents, toxicity adjusting agents, and the like, for example sodium acetate, sodium chloride, potassium chloride, calcium chloride, sodium lactate, etc. The concentrations of the antibodies according to the invention in these formulations can be varied widely, e.g. from less than about 0.01%, usually at least about 0.1%, to as much as 5% by weight, and will be selected primarily based on fluid volumes, viscosity, etc. or in accordance with the particular mode of administration selected.

Thus, a typical pharmaceutical composition for intramuscular injection could be made up to contain 1 ml sterile buffered water and about 1 to 50 mg of antibody according to the invention.

The antibodies according to the invention can be lyophilized for storage and reconstituted in a suitable carrier prior to use. Conventional lyophilization and reconstitution techniques can be employed. It will be appreciated by those skilled in the art that lyophilization and reconstitution can lead to varying degrees of biological activity loss and that use levels may have to be adjusted to compensate.

The cell line DSM ACC 2204 mentioned in the present invention which secretes the antibody Ki-4 was deposited by Boehringer Mannheim GmbH with Deutsche Sammlung von Mikroorganismen und Zellkulturen GmbH (DSM), Mascheroder Weg 1b, D-38124 Braunschweig, Germany, on Dec. 21, 1994.

EXAMPLES

Example 1

Material and Methods

Antibodies

Several established anti-CD30 mAbs were used as reference antibodies: Ki-1 which is the prototype antibody for the CD30 antigen (Schwab et al. (1982) (1)), Ber-H2 (Scbwarting et al. (1988) (14)), Mab HRS-1 and -4 from Dr. M. Pfreundschuh, Homburg, Germany, HeFi-1 (Hecht et al. (1985) (15)), antibodies M44 and M67 (Smith et al. (1993) (16)) and antibody C10 (Bowen et al. (1993) (17)).

Cell lines

The Hodgkin's disease-derived cell line L540 is described in Diehl et al. (1981) (18) with respect to the isolation of $CD30^+$ cells. L540 cells were used for immunization of BALB/c mice and for immunoprecipitation of the CD30 antigen. The immunized BALB/c spleen cells were hybridized with the non-secretor myeloma cell line X63-Ag8.653 as described (Lemke et al. (1985) (19)). The EBV-transformed B-lymphoblastoid CD30-negative cell line PDe-B-1 is described by Gatti and Leibold (1979) (20).

Production of monoclonal antibodies

BALB/c mice were immunized with L540 cells by three i.p. injections of each $10^7$ cells in intervals of 3 weeks. Hyperimmunized spleen cells of these mice (5×107) together with $10^7$ L540 cells were adoptively transferred into syngeneic recipient mice which had received a whole body X-irradiation with 6 Gy the day before. Such an adoptive cell tranfer together with the antigen into irradiated syngeneic recipients results in an enhanced frequency of antigen-specific hybridomas (Fox et al., 1981). Seven days later, the spleen cells of these mice were fused with X63-Ag8.653 myeloma cells as described (Lemke et al. (1985) (19)). The fused cells of one spleen were seeded into four 24-well fusion plates (Greiner, Nürtingen, Germany). The larger wells of these plates are subdivided at the bottom into 16 smaller compartments which ensure that the different hybridoma clones develop separately. The culture supernatant fluids of the growing hybridomas were tested for antibody activity in a cellular radio-immuno assay using I-125-radiolabeled xenogeneic goat anti-mouse antibody (GaMIg; Dianova, Hamburg, Germany) or Staphylococcal protein A (SpA; Boehringer Mannheim, Mannheim, Germany) as secondary reagents as described (Lemnke et al. (1985) (19)).

Immunohistochemistry

The specificity of the mAb was tested on human tissue specimens that had been collected during surgical operations, snap frozen in liquid nitrogen and cryopreserved at −80° C. Immunoperoxidase (Schwab et al. (1982) (1)) or immunoalkaline phosphatase methods were elaborated on 5 μ frozen sections from nearly all normal tissue types. In addition, samples of Hodgkin's disease of mixed cellularity (n=12) and nodular sclerosis (n=8) subtypes and of large anaplastic lymphoma cases (n=5) were included. Furthermore, cases of B cell lymphoma of centroblastic type and T cell lymphoma (n=5) according to the Kiel classification were studied. Non-lymphoid neoplasias included in this study, were adenocarcinomas (n=5), squamous cell carcinomas (n=3), malignant melanomas (n=8) and malignant fibrous histiocytomas (n=3). In case of antibodies recognizing a paraffine-resistant epitope, routinely processed tissue specimens, fixed in 4% formaline and embedded in paraffine were subjected to immunoperoxidase reaction following trypsin (Sigma Chemicals, München, Germany) digestion for 10 min at 37° C. In parallel studies, trypsin digestion was omitted. All cases were diagnosed in the Kiel Lymphoma registry of the German Society of Pathologists by light microscopy in H&E and Giemsa stained paraffine sections. The diagnosis was further supported by immunohistochemistry with a panel of cell lineage-specific mAb (Parwaresch et al., in preparation (22)).

Immunoprecipitation of the CD30 antigen

CD30-specific Mabs were employed to isolate the membrane antigens recognized on L540 cells. The biosynthetic labeling of L540 cells with S-35-methionine and the immunoprecipitation were as described previously Hansen et al. (1989) (2)). The specificity of the antibodies for the CD30 was tested by sequential immunoprecipitation as described (Hansen et al. (1990) (23)).

Binding inhibition studies

The experiments for determining the mutual binding inhibition of the anti-CD30 antibodies were done as described (Lemke and Hämmerling (1982) (24)). The antibodies were purified from culture supernatant fluids by affinity-chromatography either with the aid of SpA-S or GaMIg covalently coupled to CNBr-activated SEPHAROSE® CL4B (highly cross-linked 4% agarose). (Pharmacia, Freiburg, Germany). The concentration of the eluted protein was determined by the method of Whitaker and Granum (1980) (25) and the content of specific antibody was calculated as described (Lemke and Hämmerling (1982) (24)).

Results

Production of anti-CD30 antibodies

The spleen cells of two BALB/c mice immunized with L540 cells were separately fused with X63-Ag8.653 myeloma cells. The culture supernatant fluids of the growing hybridomas were sequentially tested for antibody activity against L540 cells and a CD30+ cutaneous T cell lymphoma and negativity for CD30-EBV-transformed PDe-B-1 cells and a CD30− cutaneous T lymphoma. Antibodies fulfilling these requirements were tested on paraffin-embedded and cryosections of different lymphoid tissues for a CD30 characteristic staining (see below). After these tests, the antibodies according to the invention remained, which revealed a CD30-specific staining pattern. The characteristic properties are shown in Table I.

Specificity of the antibodies

The new mAbs showed a highly restricted immunohistochemical distribution pattern in human tissue and their specificity was therefore established in further studies. With respect to normal human tissue, no reactivity was encountered in tissue samples from brain, skin, lung, heart and vessels, endocrine and exocrine glands, gastrointestinal tract, hepatobiliary system, Kidney and urogenital tract, muscles, bone, cartilage and soft tissue. Also hematopoietic cells of blood were entirely negative with these antibodies, whereas like with antibody Ki-1 a few cells in the bone marrow (Schwab et al. (1982) (1)) reacted also with antibodies Ki. In lymphoid tissues such as tonsils, lymph node and spleen, only a few lymphoid cells in the perifollicular areas showed a weak surface bound reactivity to the new antibodies. Thymus tissue was completely negative.—We also tested a large panel of permanent cell lines established from transformed human cells. The new antibodies showed an identical reactivity pattern as the established anti-CD30 antibodies Ki-1 and Ber-H2.

The immunohistochemcal analysis of a panel of non-hematopoietic human malignancies revealed that the new antibodies did not react with any of the adenocarcinomas (n=5), squamous cell carcinomas (n=3), malignant melanomas (n=8), malignant fibrous histiocytomas (n=3) and 2 cases of neurosarcomas. In case of hematopoietic neoplasias negative for CD30, no co-reactivity of these antibodies was found with acute myeloid leukemia (n=3), acute monocytic leukemia (n=3), chronic myeloid leukemia (n=3), pre-B lymphoblastoid leukemia (n=2), thymic lymphoblastoid leukemia (n=1), malignant T-lymphoma (n=5) and malignant B-lymphoma (n=3). In a panel of 18 cases of CD30-positive human lymphoma types, the monoclonal antibodies were regularly positive in a complete congruence with the reactivity of the established anti-CD30 antibodies Ki-1 and Ber-H2. The characteristic Sternberg-Reed and Hodgkin cells in nodular sklerosis or mixed cellularity type of Hodgkin's disease showed a variable reactivity with all six antibodies. In cases of Ki-1 positive large cell anaplastic lymphoma, where over 60% of the tumour cells expressed CD30, the new antibodies revealed a comparable frequency of positivity.

Properties of the anti-CD30 antibodies

In addition, the specificity of the new anti-CD30 antibodies was tested by immunoprecipitation of the recognized molecules from CD30 positive and for control purposes from negative cell lines. The results of these experiments are summarized in Table I. The antibodies allowed the isolation from positive, but not from CD30 negative cell lines of two molecules of 90 and 120 kDa respectively which most likely were identical to the 90 kDa precursor and the 120 kDa mature membrane form of the CD30 antigen (Hansen et al. (1989) (2)). The identity of the 90/120 kDa molecules isolated by the antibodies with the CD30 activation marker was confirmed by sequential immunoprecipitation, using antibodies Ki-1 and Ber-H2 as CD30-specific reference antibodies.

Binding inhibition experiments with anti-CD30 monoclonal antibodies

For the evaluation of the spatial relationship of CD30-specific determinants recognized by the various mAb on the CD30 antigen, competitive antibody-binding inhibition studies were performed. The first experiments were performed with 10 CD30-specific antibodies: Ki-4 and the established mAb Ki-1 and Ber-H2 were applied as iodinated indicators as well as non-labeled competitors, whereas mAb HRS-1 and HRSA were only available in low amounts of culture supernatant fluids and could only be employed as non-purified cold competitors.

The binding of radio-iodinated mAb Ki-1 to CD30+ Hodgkin's disease-derived L540 target cells was competed by other CD30-specific mAbs. For this, iodine-125-labeled mAb Ki-1 (0.2 µg/ml) was incubated with $2 \times 10^5$ L540 cells in the presence of different concentrations of non-labeled mAb as inhibitor in a total volume of 60 µl for 90 min at RT. In the experiment, the 100% binding value without inhibitor corresponds to 4,540 cpm bound. The binding of the Ki-1 mAb was equally well inhibited by non-labeled mAb Ki-1 and not influenced by mAb Ki-4, while it was enhanced by Ber-H2. From such binding inhibition curves, binding inhibition factors could be estimated that indicate how much more of the heterologous competitor had to be used to obtain 50% inhibition compared with the amount of cold homologous antibody which yielded 50% inhibition. These data are summarized in Table II. Lately, the mAb M44 and M67 (Smith et al. (1993) (16)) and mAb C10 (Bowen et al. (1993) (17)) were included in this study. The amounts of purified antibodies M44 and M67 were sufficient to use them as radio-labeled indicators and mAb C10 could be used as cold competitor.

The CD30-specific mAb could be divided into three groups. Group A is composed of antibodies Ki-4, Ber-H2, HRS-1 and HRS-4 which define the biggest cluster of antigen-specific epitopes on the CD30 membrane antigen. Most members of group A could mutually inhibit the binding of other members of this group to L540 target cells, but did not inhibit the binding of the other antibodies. A second group B is composed of mAb Ki-1 and M67 which displayed mutual binding inhibition to L540 target cells. Interestingly, the binding of antibodies Ki-1 was slightly enhanced by antibody Ber-H2 which belongs to group A (Table II). The third group C of CD30 specific epitopes is defined by antibodies M44, HeFi-1 and C10. These antibodies showed mutual binding inhibition to L540 cells, but their binding could not be influenced by anyone of the antibodies of groups A and B (Table II).

Influence of specific antibodies on the shedding of the CD30 membrane antigen

Anti-CD30 antibody Ki-1 enhances the shedding of the CD30 membrane antigen (Hansen et al. (1991) (7)). Since this phenomenon would counteract the toxic effects of immunotoxins, it was tested whether the anti-CD30 Mabs according to the invention influenced the shedding of this activation marker as described (Hansen et al. (1989) (2)). For this, L540 cells were pulse-labeled with S-35-methionine for 10 min, washed and resuspended in fresh medium. Then, aliquots of $2 \times 10^5$ cells were cultured for a chase period of 16 h either without antibody or mAb Ki-1, Ber-H2, Ki-4 and HeFi-1. The sCD30 was isolated as described in example 1, analyzed by SDS-PAGE (7.5–15% gradient gels under reducing conditions) and visualized by autoradiography. Compared to the negative control cultures without antibody, the release of the sCD30 was most strongly enhanced by Ki-1 and enhanced to different degrees by M44 and HeFi-1. In contrast, mAb Ber-H2 and Ki-4 clearly inhibited the release of sCD30 from L540 cells. The reduction of the sCD30 by mAb Ki-4 seemed reproducibly slightly stronger than that induced by Ber-H2.

Example 2

Isolation of sCD30 antigen

CD30-positive cells, e.g. Hodgkin-analogous L540 cells, were pulse-labelled with S-35-methionine for 10 min., followed by the removal of unincorporated material and the addition of an excess of cold methionine in fresh RPMI 1640 medium. After different periods of chasing time, the CD30 antigen was isolated either from the cells or from the supernatant fluids of those cell samples by immunoprecipitation with the aid of said anti-CD30 antibodies. The immune complexes were isolated by affinity chromatography on staphylococcal protein A-SEPHAROSE® CL-4B and the antigenic molecules were analyzed by autoradiography after separation by sodium dodecyl sulfate polyacrylamide gel electrophoresis. The quantity of the isolated sCD30 was estimated from the intensity of the labelled bands or such bands were excised from the gels and the amount of radioactivity was measured by liquid scintillation counting.

Exanmple 3

Preparation of immunotoxin (Engert et al. (1990) (6))

Immunotoxins against CD30 antigen are prepared by coupling the toxin ricin A chain on Ki-4.

For this fab fragments from Ki-4 were prepared by dialyzing the complete antibody into 0.2 mol/l citrate buffer, pH 8.0, and concentrated by ultrafiltration (Amicon™ PM-10 membrane) to 7.5 mg/ml. The pH was reduced to 3.7 by addition of 1 mol/l citric acid and the antibody solutions were subsequently incubated for 4 hours at 37° C. with pepsin (enzyme: protein ratio 1:6 by weight). The digestion was terminated by raising the pH to 8.0 with 1 mol/l Tris buffer. The f(ab')$_2$ fragments were isolated by gel filtration on columns of sephacryl™ S-200 HR equilibrated in PBS, pH 7.5. Fab'(2) fragments were reduced to Fab' monomers with 1–5 mmol/l DTT (dithiotreithol). Residual DTT was removed by gel filtration on SEPHADEX® G25 (cross-linked dextran).

IgG immunotoxins were prepared using the 4-succinimidyloxycarbonyl-α-methyl-(2-pyridyl dithio) toluene linking agent described by Thorpe et al. (1987) (26).

Fab' immunotoxins were prepared according to the method of Ghetie et al. (1988) (27). Briefly, Fab' fragments (5 mg/ml in 0.1 mol/l sodium phosphate buffer, pH 7.5, containing 1 mmol/l EDTA) were derivatized with 5.5'-dithiobis(2-nitroberzoic acid) at a final concentration of 2 mmol/l (Ellman's reagent). Unreacted Ellman's reagent was removed by gel filtration on a SEPHADE X® G25 column equilibrated in PBS. Derivatized Fab' fragments which contained 1–2 activated disulfide groups were allowed to react with a 1.5-fold molar excess of freshly reduced A chain for 2 hours at room temperature. The Fab' dgA immunotoxins were subsequently purified on SEPHADEX® S200 HR (molecular sieve based on a highly cross-linked dextran) and BLUE SEPHAROSE® G25 (highly cross-linked polysaccharide to which a blue triazine dye is bound) columns as described by Thorp et al. (1987) (26).

TABLE I

Properties of monoclonal anti-CD30 antibody Ki-4

| Designation of anti-CD30 antibodies | Isotype | Protein A binding | $M_r$ sCD30[a] | Reaction with antigen | | |
|---|---|---|---|---|---|---|
| | | | | cryo- sections | detection of antigen paraffin-embedded sections | |
| | | | | | without | plus trypsin |
| Ki-4 | γ1, κ | — | 90/120[b] + | + | + | + |

[a]It was tested whether the antibody could isolate the soluble form of the CD30 (sCD30) from culture supernatant fluids of Hodgkin's disease-derived L540 cells which had been labelled with $^{35}$S-methione.
[b]Numbers indicate the molecular weights of the immunoprecipitated different forms of the CD30.

TABLE II

Binding inhibition of iodine-125-labelled anti-CD30 antibodies by non-radiolabelled antibodies[a]

| | Iodine-125-labelled anti-CD30 antibodies | | | | | |
|---|---|---|---|---|---|---|
| | Cluster A | | Cluster B | | Cluster C | |
| Inhibitor[b] | Ki-4 | Ber-H2 | Ki-1 | M67 | M44 | HeFi-1 |
| Ki-4 | 1[c] | 3[d] | – | – | – | – |
| Ber-H2 | 0.5 | 1 | –[e] | – | – | – |
| HSR-1 | – | +[f] | – | – | – | – |
| HSR-4 | + | + | – | .[h] | . | . |
| Ki-1 | – | – | 1 | 13 | – | – |
| M67 | . | . | . | 1 | . | . |
| M44 | . | . | . | . | 1 | . |
| HeFi-1 | – | – | – | – | 3.9 | 1 |
| C10 | . | . | . | . | +++[i] | +++[i] |

[a]Assay was done with Hodgkin's disease-derived CD30+ L540 cells.
[b]Antibodies HSR-1 and -4 were only available in low amounts as non-purified culture supernatant fluids. The amounts of purified M44 and M67 allowed the application as radio-labelled indicator, but not as non-labelled competitors.
[c]The amount of homologous antibody that gave 50% inhibition is set 1.
[d]Numbers indicate the factor by which the homologous binding inhibition value 50% has to be increased to obtain 50% inhibition with the heterologous antibody.
[e]No significant inhibition.
[f]Significant inhibition was observed at high concentrations of heterologous antibody, but 50% inhibition was not reached.
[h]. = not tested.
[i]+/+++ = Antibody C10-containing ascites fluid induced 45% inhibition of radiolabelled antibody Ki-3 (+) and complete inhibition of antibodies M44 and HeFi-1 (+++).

References (1) Schwab et al., Nature 299 (1982) 65–67
(2) Hansen et al., Biol. Chem. Hoppe-Seyler 370 (1989) 409–416
(3) Josimovic-Alasevic et al., Eur. J. Immunol. 19 (1989) 157–162
(4) Pfreundschuh et al., Int. J. Cancer 45 (1990) 869–874
(5) Pizzolo et al., Br. J. Haematol. 75 (1990) 282–284
(6) Engert et al., Cancer Research 50 (1990) 84–88
(7) Hansen et al., Immunobiol. 183 (1991) 214
(8) Froese et al., J. Immunol. 139 (1987) 2081–2087
(9) G. Pallesen, Histopathology 16 (1990) 409–413
(10) R. Schwarting et al., Blood 74 (1989) 1680
(11) Press et al., J. Immunol. 141 (1988) 4410–4417
(12) May et al., J. Immunol. 144 (1990) 3637–3642
(13) P. Rothman et al., Mol. Cell. Biol. 10 (1990) 1672–1679
(14) Schwarting et al., Blood 74 (1988) 1678–1689
(15) Hecht et al., J. Immunol. (1985) 4231–4236
(16) Smith et al., Cell 73 (1993) 1349–1360
(17) Bowen et al., J. Immunol. 151 (1993) 5896–5906
(18) Diehl et al., J. Cancer Res. Clin. Oncol. 101 (1981) 111–124
(19) Lemnke et al., Eur. J. Immunol. (1985) 442–447
(20) Gatti and Leibold, Tissue Antigens 13 (1979) 35–44

(21) Fox et al., Eur. J. Immunol. (1981) 431–434
(22) Parwaresch et al., in preparation
(23) Hansen et al., Res. Immunol. (1990) 13–31
(24) Lermke and Hämmerling, J. Immunol. 128 (1982) 2465–2469
(25) Whitaker and Granum, Anal. Biochem. 109 (1980) 156–159
(26) Thorpe et al., Cancer Research 47 (1987) 5924–5934
(27) Ghetie et al., Cancer Research 48 (1988) 2610–2617
(28) I. Pastan et al., WO 92/07271
(29) I. Pastan et al., WO 90/12592
(30) Brinkrnann et al., Proc. Natl. Acad. Sci. USA 88 (1991) 8616–8620
(31) Pastan et al., Cancer Res. 51 (1991) 3781–3787
(32) FitzGerald and Pastan, J. Natl. Cancer Inst. 81 (1989) 1455–1461
(33) Bonino et al., BFE 9 (1992) 719–723
(34) Holliger et al., Proc. Natl. Acad. Sci. USA 90 (1993) 6444–6448
(35) Holliger and Winter, Current Opin. Biotechnol. 4 (1993), 446–449
(36) R. Scopes, Protein Purification, Springer Verlag, N.Y. (1982)
(37) E. A. Kabat et al., Sequences of Proteins of Immunological Interest (1987), National Institute of Health, Bethesda Md.
(38) Glassy and Dillman, Mol. Biother. 1 (1988) 7–13
(39) Morrison, Annu. Rev. Immunol. 10 (1992) 239–265
(40) Winter and Milstein, Nature 349 (1991) 293–299
(41) Borrebaeck et al., Proc. Natl. Acad. Sci. USA 85 (1988) 3995–3999
(42) Borrebaeck, Immunol. Today 9 (1988) 355–359
(43) Griffith et al., EMBO J. 12 (1993) 725–734
(44) Brüggemann et al., J. Exp. Med. 166 (1987) 1357–1361
(45) E. Harlow and D. Lane, Antibodies: A Laboratory Manual, Cold Spring Harbor Press (1988)
(46) Bessler et al., Immunobiol. 170 (1985) 239–244
(47) Jung et al., Angewandte Chemie 97 (1985) 883
(48) Cianfiglia et al., Hybridoma Vol. 2 (1993) 451–457
(49) Brinkmann et al., PNAS 89 (1992) 3075–3079
(50) Brinkmann et al., PNAS 90 (1993) 7538–7542
(51) WO 88/09344
(52) WO 88/01649
(53) EP-B 0 193 276
(54) U.S. Pat. No. 7,648,971
(55) U.S. Pat. No. 4,952,496
(56) U.S. Pat. No. 6,595,016
(57) Houston et al., PNAS USA 85 (1988) 5879–5883
(58) Bird et al., Science 242 (1988)
(59) Hood et al., Immunology, Benjamin N.Y., 2nd edition (1984)
(60) Hunkapiller and Hood, Nature 323 (1986) 15–16
(61) Proteins, Structures and Molecular Principles, Creighton (editor), W. H. Freeman and Company, New York (1984)
(62) Introduction to Protein Structure, C. Brandon and J. Tooze, Garland Publishing, New York (1981)
(63) Thornton et al., Nature 354 (1991) 105
(64) Sambrook et al., Molecular Cloning: A Laboratory Manual, 2nd edition (1989), Cold Spring Harbor, N.Y.
(65) Berger and Kimmel, Methods in Enzymology, Vol. 152, Guide to Molecular Cloning Techniques (1987), Academic Press Inc., San Diego, Calif.

We claim:

1. An antibody obtained from the cell line deposited at the Deutsche Sammlung von Mikroorganismen und Zellkulturen GmbH (DSM) under accession number ACC 2204.

2. An antigen binding fragment of the antibody obtained from the cell line deposited at the Deutsche Sammlung von Mikroorganismen und Zellkulturen GmbH (DSM) under accession number ACC 2204.

3. The antigen binding fragment of claim 2 wherein said fragment is selected from the group consisting of a Fab, a Fab', and a (Fab')$_2$ fragment.

4. A polypeptide comprising a) an antibody of claim 1, and b) a toxin conjugated thereto.

5. A polypeptide comprising a) an antigen binding fragment of claim 2, and b) a toxin conjugated thereto.

6. A chimeric antibody comprising a) the variable region of an antibody from the cell line deposited at the Deutsche Sammlung von Mikroorganismen und Zellkulturen GmbH (DSM) under accession number ACC 2204 and b) the constant region of a human antibody, wherein the antibody has reduced immunogenicity in humans.

7. A humanized antibody comprising a) the six complementarity determining regions (CDR) of the antibody from the cell line deposited at the Deutsche Sammlung von Mikroorganismen und Zellkulturen GmbH (DSM) under accession number ACC 2204, b) non-CDR variable regions from human variable regions, and c) the constant region of a human antibody, wherein the antibody has reduced immunogenicity in humans.

8. The cell line that is deposited at Deutsche Sammlung von Mikroorganismen und Zellkulturen GmbH (DSM) under accession number ACC 2204.

9. A process for the production of an antibody which binds to the CD30 antigen, comprising the steps of:

a) culturing the cell line that is deposited at Deutsche Sammlung von Mikroorganismen und Zellkulturen GmbH (DSM) under accession number ACC 2204; and b) producing and isolating an antibody from said cell line.

10. A composition comprising the antibody of claim 1 and a pharmaceutically acceptable excipient.

11. A composition comprising the antibody fragment of claim 2 and a pharmaceutically acceptable excipient.

12. A method for the detection of Hodgkin's disease, comprising the steps of:

a) contacting a biological sample with an antibody or antibody fragment which binds to the CD30 antigen, wherein said antibody or antibody fragment is obtainable from the cell line deposited at the Deutsche Sammlung von Mikroorganismen und Zellkulturen GmbH (DSM) under accession number ACC 2204, under conditions such that said antibody or antibody fragment binds to CD30 antigen present in said biological sample, b) detecting any antibody bound to CD30 antigen, and c) correlating antibody bound to CD30 as an indication of Hodgkin's disease.

13. A process for the production of an antibody with a reduced immunogenicity in humans comprising manipulating an antibody obtained from the cell line deposited at the Deutsche Sammlung von Mikroorganismen und Zellkulturen GmbH (DSM) under accession number ACC 2204, to produce an antibody comprising a) the variable region of an antibody from the cell line deposited at the Deutsche Sammlung von Mikroorganismen und Zellkulturen GmbH (DSM) under accession number ACC 2204 and b) the constant region of a human antibody.

14. A pharmaceutical composition comprising the antibody of claim 6 and a pharmaceutically acceptable excipient.

15. A pharmaceutical composition comprising the antibody of claim 7 and a pharmaceutically acceptable excipient.

16. A pharmaceutical composition comprising the polypeptide of claim 5 and a pharmaceutically acceptable excipient.

* * * * *